US00PP18166P2

(12) United States Plant Patent
Boeder

(10) Patent No.: US PP18,166 P2
(45) Date of Patent: Oct. 30, 2007

(54) ***CHRYSANTHEMUM* PLANT NAMED 'LYDIA'**

(50) Latin Name: ***Chrysanthemum morifolium* L.**
Varietal Denomination: Lydia

(75) Inventor: Mark Roland Boeder, The Hague (NL)

(73) Assignee: Chrysanthemum Breeders Association, N.V., Aalsmeer (NL)

( * ) Notice: Subject to any disclaimer, the term of this patent is extended or adjusted under 35 U.S.C. 154(b) by 0 days.

(21) Appl. No.: 11/403,930

(22) Filed: Apr. 14, 2006

(51) Int. Cl.
*A01H 5/00* (2006.01)

(52) U.S. Cl. ..... Plt./289
(58) Field of Classification Search ..... Plt./289
See application file for complete search history.

*Primary Examiner*—Kent Bell
*Assistant Examiner*—S. B. McCormick-Ewoldt
(74) *Attorney, Agent, or Firm*—Steptoe & Johnson LLP

(57) ABSTRACT

A *chrysanthemum* plant named 'Lydia' characterized by its medium sized blooms with yellow ray florets and a yellow center, with prolific branching; blooming for a period of 5 weeks.

3 Drawing Sheets

Latin name of the genus species: *Chrysanthemum morifolium* L.

BACKGROUND OF THE INVENTION

'Lydia' is a product of a breeding and selection program for outdoor pot mums (garden mums) which had the objective of creating new *chrysanthemum* cultivars with a decorative type flower, a natural flowering date late in autumn; blooming for a period of 5 weeks. The new plant of the present invention comprises a new and distinct cultivar of *chrysanthemum* plant; 'Lydia' is a seedling resulting from a crossing program, set up by a previous breeder, and which records are unknown to the inventor. The new and distinct cultivar was discovered and selected as a flowering plant by Mark Roland Boeder on a cultivated field in Rijsenhout, The Netherlands in 2001. The first act of asexual production of 'Lydia' was accomplished when vegetative cuttings were taken from the initial selection in 2001 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* (grown indoor) is shown in the accompanying drawings, the color being as nearly true as possible with color photographs of this type.

DESCRIPTION OF THE INVENTION

Figure 1:
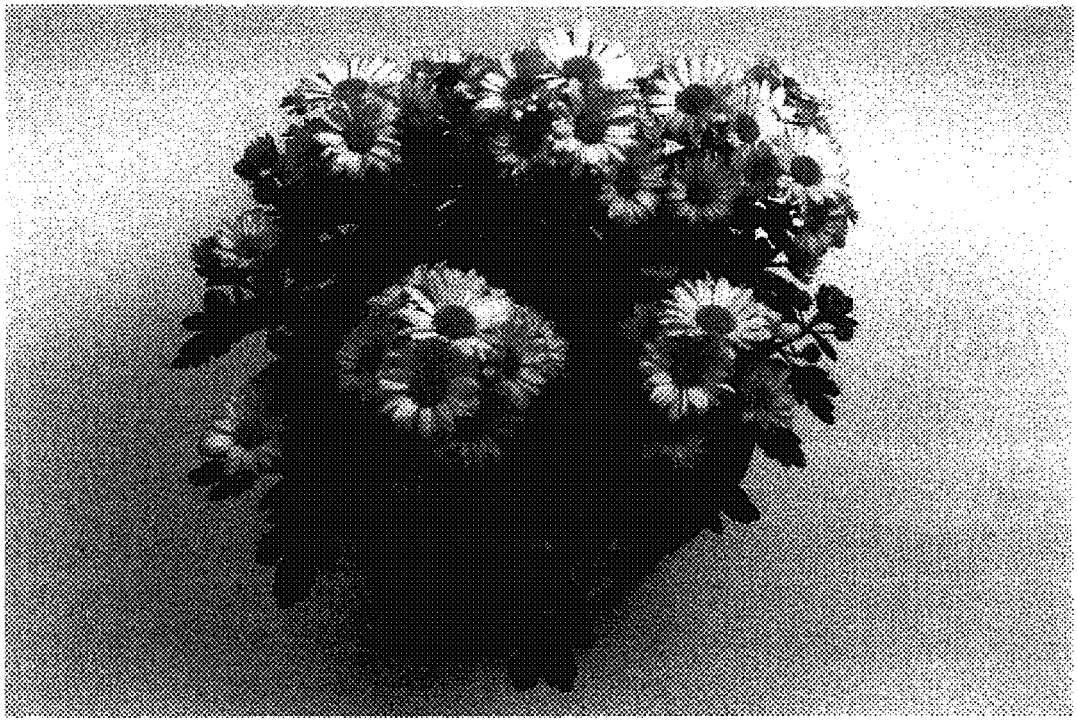
FIG. 1 shows a plant of the cultivar in full bloom.
Figure 2:
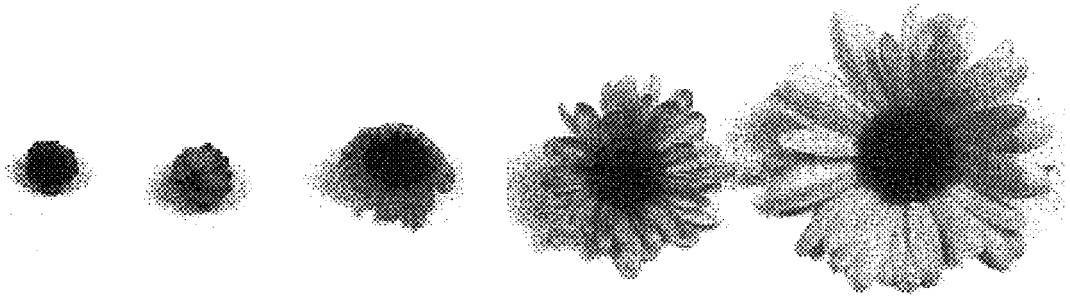
FIG. 2 shows the various stages of bloom of the new cultivar.
Figure 3:
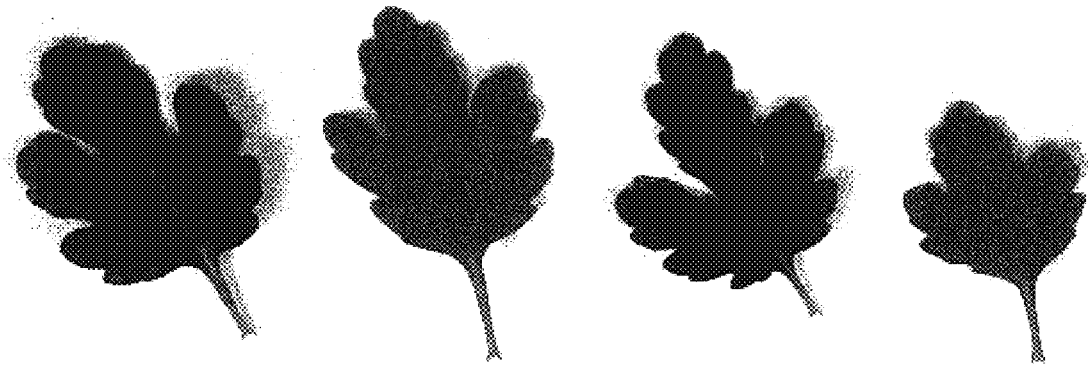
FIG. 3 shows the various stages of foliage of the new cultivar.

This new variety of *chrysanthemum* is of the botanical classification *Chrysanthemum morifolium* L. The observations and measurements were gathered from plants grown indoor in a greenhouse in Rijsenhout, The Netherlands; a complete analysis of the performance outdoor has not yet been made. After rooting, one cutting was planted in a container of 18 cm diameter in week 1 in 2006. Short-day treatment of 11L:13D started in week 5. Temperature of the greenhouse ranges from 18 to 22° C.; growth retardant alar was supplied at a dose of 1 g/l in week 8. The average height of the plants was 18 cm. No tests were done on disease or insect resistance or susceptibility. No tests were done on cold or drought tolerance. This new variety produces medium sized blooms with yellow ray florets and a yellow center.

From the cultivars known to inventor the most similar existing cultivar in comparison to 'Lydia' is "Cronus" (U.S. Plant Pat. No. 14,563). When "Cronus" and 'Lydia' are being compared the following difference is noticed: The difference of "Cronus" and 'Lydia' are (1) Natural season blooming date. (2) Flower type. And (3) Color ray florets. (1) Plants of 'Cronus' flower in early autumn, while those of 'Lydia' in late autumn. (2) Plants of 'Cronus' have double type flowerheads, while 'Lydia' flowers are of single type. (3) The ray florets of 'Lydia' are more pale yellow than those of 'Cronus'.

The following is a description of the plant and characteristics that distinguish 'Lydia' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *chrysanthemum* plant 'Lydia' (when grown indoor)

| | |
|---|---|
| Bud | |
| Size | Small; cross-section 0.5 cm, height 0.3 cm |
| Outside Color | Green 143A |
| Phyllaries | 2 rows, length 7 mm, width 3 mm |
| Phyllaryies among disc-florets | Not present |
| Bloom | |
| Type | Single |
| Height | 1 cm |
| Size | 4 cm |
| Phyllary number | 22 |

TABLE 1-continued

Botanical Description of *chrysanthemum* plant 'Lydia' (when grown indoor)

| | |
|---|---|
| Phyllary color | Green 138A |
| Phyllary length and width | 0.3 cm and 0.1 cm |
| Peduncle length | 2.5-3 cm |
| Peduncle color | Green N138C |
| Number of blooms per branch | Approx. 10 blooms per branch |
| Performance on the plant | 5 weeks |
| Seeds | Produced in small quantities, ovate grey-brown 199A, 1½ mm in length. |
| Fragrance | Typical *chrysanthemum*, slightly |
| Color | |
| Center of the flower (disc florets) | Immature Green-yellow 1B with a Yellow-green N144C dot<br>Mature Yellow 13A |
| Color of upper surface of the ray-florets | Yellow 10A |
| Color of the lower surface of the ray-florets | Yellow 10C |
| Tonality from Distance | A garden mum with yellow flowers |
| Color of the ray-florets after aging of the plant | Yellow 10B |
| Ray florets | |
| Texture | Upper and under side smooth |
| Number | 36-38 |
| Cross-section | Flat |
| Longitudinal axis of majority | Straight |
| Length of corolla tube | 0.4 cm |
| Ray-floret margin | Entire |
| Ray-floret length | 3 cm |
| Ray-floret width | 0.5 cm |
| Ratio length/width | High |
| Shape of tip | Rounded |
| Disc florets | |
| Disc diameter | 1.5 cm |
| Distribution of disc florets | Numerous, clearly visible in all stages |
| Shape | Tubular |
| Color | Yellow 11D at base |
| Receptacle shape | Conical raised |
| Reproductive Organs | |
| Stamen | Present in disc florets only |
| Stamen color | Yellow-green 114A |
| Pollen | Present |
| Pollen color | Yellow 7A |
| Styles | Thin |
| Style color | Yellow 13A |
| Style Length | 0.3 cm |
| Stigma color | Yellow-green 144A |
| Stigma Width | 1 mm |
| Ovaries | Enclosed in calyx |
| Plant | |
| Form | Grown as a spray type potmum, mounded and round |

TABLE 1-continued

Botanical Description of *chrysanthemum* plant 'Lydia' (when grown indoor)

| | |
|---|---|
| Growth habit | Spherical shape |
| Growth rate | Vigorous |
| Height | 18 cm |
| Width | 30 cm |
| Stem Color | Green 138 A-B |
| Stem Strength | Medium |
| Stem Brittleness | Not brittle |
| Stem Anthocyanin Coloration | Absent |
| Internode length | 0.5-1.5 cm |
| Length of lateral branch | From top to bottom 12 cm |
| Lateral branch color | Green 138B |
| Lateral branch, attachment | Medium strength |
| Branching (average number of lateral branches) | Prolific with 10 breaks after pinching |
| Flowering response | 7 weeks |
| Foliage | |
| Leaf color | Upper side Yellow-green 147A<br>Lower side Green N138 |
| Color midvein | Upper side Yellow-green 147D<br>Lower side Yellow-green 148D |
| Size | Small; length 6 cm, width 3.5-4 cm |
| Quantity (number per lateral branch) | 15 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronate |
| Petiole length | 1.5-2 cm |
| Petiole color | Yellow-green 147D |

TABLE 2

Differences with the comparison variety

| Plant characteristic | 'Lydia' | 'Cronus' |
|---|---|---|
| Natural season blooming date | Late autumn | Early autumn |
| Flowerhead type | Single | Double |
| Color ray-florets (grown indoor) | Yellow 10A | Yellow 12A |

I claim:

1. A new and distinct variety of *chrysanthemum* plant as described and illustrated.

* * * * *